United States Patent
Heinz et al.

(10) Patent No.: US 6,719,141 B2
(45) Date of Patent: Apr. 13, 2004

(54) TRANSPORT DEVICE FOR MEDICINAL CONTAINERS

(75) Inventors: Jochen Heinz, Vendersheim (DE); Michael Spallek, Ingelheim (DE); Arthur Fabian, Mainz (DE)

(73) Assignee: Schott Glas, Mainz (DE)

( * ) Notice: Subject to any disclaimer, the term of this patent is extended or adjusted under 35 U.S.C. 154(b) by 24 days.

(21) Appl. No.: 09/804,438

(22) Filed: Mar. 12, 2001

(65) Prior Publication Data

US 2001/0052476 A1 Dec. 20, 2001

(30) Foreign Application Priority Data

Mar. 15, 2000 (DE) .......................... 100 12 575

(51) Int. Cl.⁷ ................................ B65D 1/34
(52) U.S. Cl. ..................... 206/563; 206/443; 206/446
(58) Field of Search ................ 206/363, 364, 206/365, 366, 446, 477, 475, 480, 486, 562, 563, 565

(56) References Cited

U.S. PATENT DOCUMENTS

| | | | |
|---|---|---|---|
| 3,643,812 A | | 2/1972 | Mander et al. |
| 3,781,120 A | * | 12/1973 | Engelhardt ............. 215/DIG. 3 |
| 4,774,772 A | | 10/1988 | Vetter |
| 4,798,292 A | * | 1/1989 | Hauze ......................... 206/439 |
| 4,928,821 A | * | 5/1990 | Belko, Jr. ................... 206/486 |
| RE34,133 E | * | 11/1992 | Thorne ......................... 422/99 |
| 5,185,985 A | | 2/1993 | Vetter et al. |
| 5,291,997 A | * | 3/1994 | He et al. ..................... 206/366 |
| 5,392,914 A | * | 2/1995 | Lemieux et al. ............ 206/486 |
| 5,398,803 A | | 3/1995 | Neber |
| 5,452,810 A | * | 9/1995 | Schwartz .................... 206/446 |
| 5,487,997 A | * | 1/1996 | Stolp .......................... 436/54 |
| 5,516,490 A | | 5/1996 | Sanadi ....................... 422/101 |
| 5,582,594 A | * | 12/1996 | Chen .......................... 604/110 |
| 5,714,127 A | * | 2/1998 | DeWitt et al. .............. 422/130 |
| 5,720,226 A | * | 2/1998 | Padovano ..................... 108/25 |
| 5,823,363 A | * | 10/1998 | Cassel ......................... 206/366 |
| 5,950,832 A | * | 9/1999 | Perlman ...................... 206/446 |
| 5,975,295 A | * | 11/1999 | Diamond ..................... 206/366 |
| 6,012,595 A | | 1/2000 | Thilly |
| 6,286,678 B1 | * | 9/2001 | Petrek ......................... 206/443 |
| 6,419,086 B1 | * | 7/2002 | Vecchio ...................... 206/366 |

FOREIGN PATENT DOCUMENTS

| | | |
|---|---|---|
| DE | 36 13 489 C2 | 2/1989 |
| DE | 40 21 836 C1 | 5/1991 |
| DE | 42 43 786 A1 | 7/1994 |
| EP | 0 790 063 A1 | 8/1997 |
| EP | 0 976 453 A2 | 2/2000 |
| WO | 94/14484 | 7/1994 |

OTHER PUBLICATIONS

Tokyo Pack 1992, Packstoffentwicklungen in Huelle Und Fuelle, Neue Verpackung 12/92, pp. 32–36.

* cited by examiner

*Primary Examiner*—Shian Luong
(74) *Attorney, Agent, or Firm*—Michael J. Striker (57) ABSTRACT

The device for transporting, filling and sterilizing medicinal containers (3) includes a rigid foamed plastic carrier plate (1) provided with a plurality of first openings (2) for receiving the respective containers (3). The first openings have respective open cross-sections adapted to corresponding cross-sections of the containers and the rigid carrier plate (1) has a predetermined thickness, so that the containers (3) are clamped and held fixed in position relative to the carrier plate and centered in the first openings (2) without rattling so that no scratch marks and/or no static charges are produced on the medicinal containers (3) during transport. The rigid foamed plastic carrier plate (1) is provided with a pore-free sealed surface that facilitates sterilization. Second openings (20), which are smaller than the first opening (2) and cannot receive the containers, are also provided in the carrier plate to facilitate sterilization in an autoclave.

5 Claims, 6 Drawing Sheets

TRANSPORT DEVICE FOR MEDICINAL CONTAINERS

BACKGROUND OF THE INVENTION

1. Field of the Invention

The present invention relates to a transport device for medicinal containers, which has a carrier member made from plastic that is provided with a plurality of openings for receiving the respective containers.

2. Prior Art

Medicinal containers, especially packing means for medically effective ingredients, such as ampoules, flasks, bottles, injection molded ampoules, glass cylinders, syringe bodies, filled syringes (finished syringes) made from glass or plastic and capsules are known and on the market.

These medicinal containers typically have a circular cross-section. However they can also have a polygonal cross-section.

These types of containers are usually first made in a glass and/or plastic processing factory and then transported to a pharmaceutical plant, in which they are filled. A series of processing steps, such as washing, sterilizing, packing, transporting, siliconizing, packaging, etc., are required both in the manufacture of the containers and also in their filling.

The handling, transporting and storage of these types of medicinal containers present special problems, such as those encountered in filling and unfilling syringes, syringe bodies, cylindrical ampoules. The essential reason is that these containers are mass-produced articles. In as much as they are mass-produced they are not prepared and handled individually. Instead they are handled only automatically or mechanically in orderly batches and/or magazined in so-called trays for economic reasons.

Many embodiments of suitable devices are known. DE 42 43 786 A1 discloses devices for transporting objects, especially tubes, e.g. cylinders for syringes, finished syringes and the like made from glass, plastic or the like. These devices have a circular circumferential carrier, which is provided with a plurality of outwardly opening receptacles for the individual objects, which are spaced from each other in succession along its outer edge. The individual objects can be held in or removed from the receptacles in the carrier. Each receptacle or receptacle pair comprises a clamping device, by means of which a respective object can be clamped or held therein.

EP 0 790 063 A1 discloses a frame or housing module with a plurality of clip-like clamping devices for holding syringe bodies vertically.

DE 40 21 836 C1 describes an apparatus for handling injector or syringe cylinders, which comprises a series of complex metal parts, such as supporting and locking or fixing plates. Both plates are arranged over each other with through-going openings in the respective plates for holding the injector or syringe cylinders aligned with each other.

A similar device is described in DE 36 13 489 C2.

The above-described transport device has grave disadvantages. It is not equally suitable without further modification for glass and plastic containers, since the preponderantly used metallic materials can easily lead to scratching plastic bodies, for one thing. For another, they are not suitable for one-time uses because of their high cost, their high weight and so forth and must be subjected to an arduous or expensive cleaning process prior to use in clean rooms. During the filling of finished syringe, which must be supplied in sterile form, the empty containers are introduced into the filling machine with the above-described transport device. For filling, i.e. for insertion of the filling tube into the syringe, and for subsequently inserting the charging tube in the syringe filled with fluid, it must be exactly aligned geometrically in a special step, since the housing is not reliably held in this alignment. This alignment is above all important in placing the injector piston in the syringe, since the charging tube preferably has a diameter, which is only slightly smaller than the syringe body.

A comb-like holder specially designed for a glass syringe, which is exclusively suitable for glass syringes with finger supports, is described in WO 94/14484. The syringes are also not centered in this holder, but are freely suspended from their finger supports.

Plastic perforated plates, in which the glass syringes, suspended on their finger supports, are held loosely, in the state of the art HYPAK® SCF® system are described in the above-mentioned EP 0 790 063 A1. A special centering process is required in this system.

An additional disadvantage of these holders for glass syringes freely suspended from their finger supports is that the alignment or arrangement of the syringes with respect to their finger supports changes during transport. The syringe bodies can vibrate very easily during transport because they are secured comparatively loosely. Thus they are easily contaminated. Furthermore contaminating particles are rubbed off the syringe bodies by the strong shaking or vibrating motions during transport and can be conveyed into the syringe bodies. Finally the completely filled holder has a certain deformation, which is disadvantageous for the filling process.

SUMMARY OF THE INVENTION

It is an object of the present invention to provide a transport device for medicinal containers of the above-described type, which can be made in a very simple manner and is universally useable, and which guarantees secure vibration-free and/or rattle-free holding and transport of the containers.

According to the invention the device for transporting medicinal containers includes a rigid plastic carrier plate provided with a plurality of openings for receiving the medicinal containers. These openings have respective open cross-sections adapted to corresponding cross-sections of the medicinal containers and the carrier plate has a predetermined thickness, so that the medicinal containers are clamped and held fixed and centered in the openings when received in them and so that no scratch marks are produced on the medicinal containers during transport.

The clamping of the containers in the openings is such that they do not vibrate and/or rattle during transport. No static charge is produced on the container during transport because of that aspect of the invention, i.e. the containers remain particle-free without the static charge and remain in the position in which they were inserted during transport. This is particularly advantageous for performing subsequent processing. Particularly no subsequent centering of the containers is required, for example for filling, so that the filling can occur in the transporting device.

In a preferred embodiment of the invention the carrier plate is made of a stiff plastic material and causes no scratch tracks on the container wall during insertion and withdrawal of the containers from the openings.

According to a preferred embodiment, the carrier plate is made from foamed plastic material, preferably foamed polypropylenes (PP) or foamed polyesters (PET). Carrier plates made in this way are very economical. The carrier plates can be recyclable through-away articles so that costly and arduous cleaning can be eliminated. Although the foamed carrier plate already has great rigidity, it can have reinforcing or stiffening elements or a rib structure when it has larger dimensions.

Preferably the carrier plate has at least one pore-free sealed surface. The carrier plate with the containers in it can be sterilized in an autoclave when it has a pore-free sealed surface.

In preferred embodiments of the device for transporting the medicinal containers the openings are arranged in rows in the carrier plate. In order to obtain a high packing density, adjacent rows are displaced or shifted with respect to each other by one half a distance between neighboring holes in one of the adjacent rows.

In order to provide especially reliable and secure clamping of the container in the carrier plate, a number of different preferred embodiments are conceivable.

Particularly secure seating of the containers in the carrier plate is obtained when the openings are through-going conical passages through the carrier plate and the through-going conical passages are tapered so that the through-going conical passages are narrowest on one side or the other of the carrier plate.

Alternatively respective collars projecting from the carrier plate are formed around corresponding openings. Parts of the containers, such as finger supports of syringes, can rest on the collars.

In another embodiment two radially inwardly extending annular constricting portions are arranged spaced axially from each other within each of the openings. These constricting portions engage and hold the containers inserted in the openings.

It is also conceivable to provide another embodiment in which the carrier plate is provided with three edge elements respectively at different heights within each of the openings in order to provide a three point support for the medicinal containers when the medicinal containers are received in the openings. This improves the self-centering action and prevents thermal isolation of part of the container, which is helpful for sterilization procedures.

The reliable fixing of the containers securely in the openings has the advantage that a static charge which will attract dirt and other particles does not develop on the containers due to relative motion between the containers and the carrier plate (nest).

Furthermore the reliable securing of the containers prevents damage or penetration of the sealing foil which closes the entire magazine, which can occur because of the unavoidable shaking or rattling during transportation. Thus desterilization is reliably prevented. In order to prevent this desterilization with the current device for transporting the medical containers an intervening foam or foil is used, which is superfluous now because of the structure of the carrier plate according to the invention.

The transport or carrier plate, in as much as it guarantees vibration-free and/or rattle-free transport of the containers, can be used in direct filling of the containers. In contrast the current practice is to lift the containers individual or in groups from the nest and to perform an arduous centering and alignment of the container prior to filling. These latter steps are advantageously eliminated when the carrier plate according to the invention is used. A considerably higher filling throughput can be obtained with the nest according to the invention in contrast to the state of the art.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENTS

The device according to the invention for transporting medicinal containers 3 comprises a one-piece rigid rectangular carrier plate 1 made from foamed plastic, preferably foamed polypropylene (PP), foamed polyester (PET) or similar plastic materials, as described in the report for Tokyo Packing 1992 in "New Packaging", December, 1992, pp. 32 to 38, which is incorporated by reference in the present disclosure.

The dimensions of the carrier plate 1 are adapted to or are determined by the unit, in which the carrier plate is held during transport. The rectangular carrier plate of the art usually has a dimension of about 20 cm×25 cm, with a thickness of about 1 to 2 cm. Larger carrier plates with dimensions of up to 100×100 cm with a thickness of 1 to 2 cm can be used for handling a larger number of containers.

Figure 1:
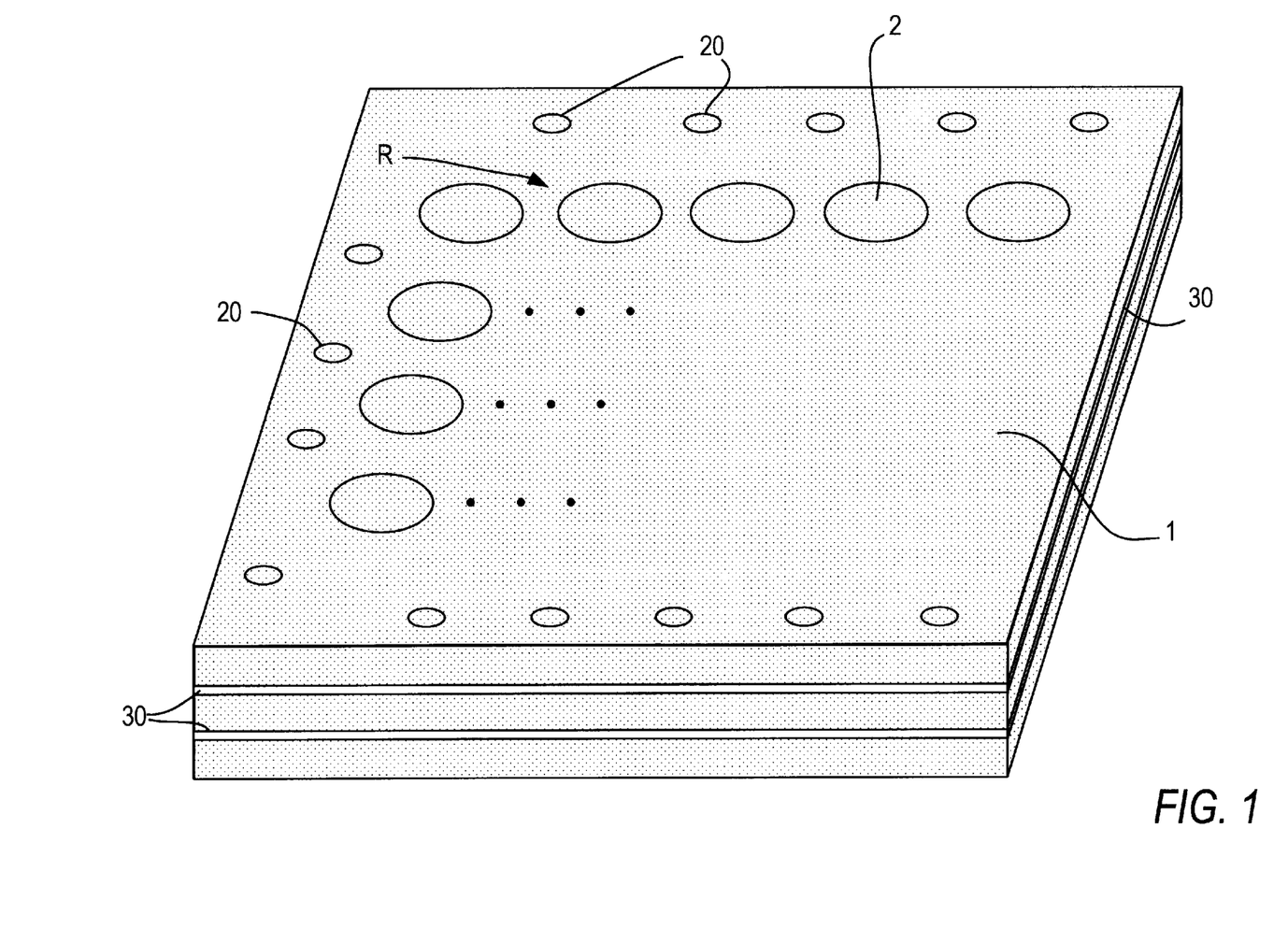
FIG. 1 is a diagrammatic perspective view of the basic structure of a carrier plate according to the invention for collective transport of medicinal containers.

Circular or rectangular or square openings 2 are provided in the carrier plate 1 for receiving the medicinal containers 3 (FIG. 2) in several rows, of which only one, R, is completely illustrated in FIG. 1. The embodiment of the carrier plate 1 shown in FIG. 1 is provided with circular through-going openings 2 for the containers 3 with cylindrical container walls. These through-going openings 2 are already formed for this purpose during manufacture of the carrier plate 1. They could however in principle be bored by a suitable multiple hole boring module after first manufacturing the carrier plate.

If the container cross-section is not circular, but e.g. triangular, then the openings 2 should have a corresponding cross-section.

Preferably the carrier plate 1 is formed so that it has a pore-free surface. This happens by a subsequent surface treatment of the foamed plastic carrier plate 1.

The diameter of the through-going openings 2 is thus selected to correspond to the diameter of the containers 3, so that each container 3 is clamped and held fixed and centered in each opening 2. The transport plate 1 according to the invention thus, because of these features, prevents relative axial motion between the containers 3 and the carrier plate 1 and thus is suitable for scratch-sensitive containers, such as container made from brittle plastic materials.

The carrier plate 1 according to the invention can—when it has a closed pore surface—be autoclaved advantageously with empty or filled containers, so that no "unloading" of containers is required for this sterilization step.

Figure 2A:
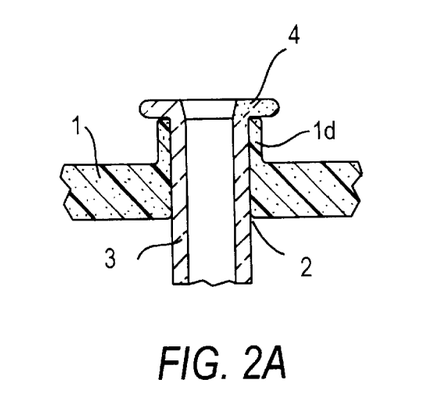
FIGS. 2A, 2B, 2C, 2D and 2E are respective cutaway cross-sectional views through five different embodiments of the carrier plate of the invention with respective different clamping seats for containers in the form of syringes with finger supports held in through-going holes provided in the carrier plates, in which the finger supports protrude above the carrier plate.

FIG. 2A shows the receipt of a container 3 shaped like a syringe body, which has an upper finger support 4, in the carrier plate 1. The carrier plate 1 has a circumferential collar 1d around the through-going opening 2, on which the finger support 4 rests, slightly raised. The through-going opening 2 is cylindrical.

Figure 2B:
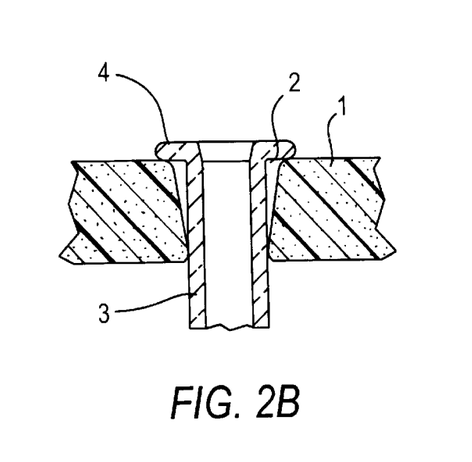
Figure 2C:
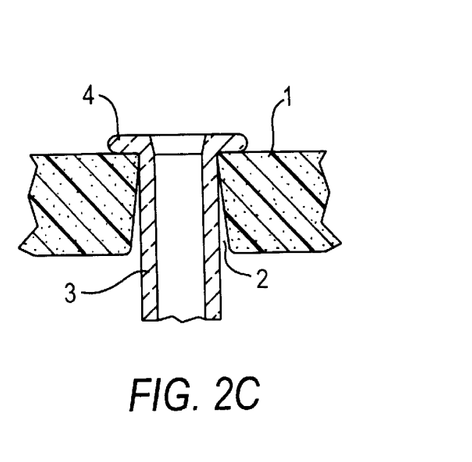
Figure 3A:
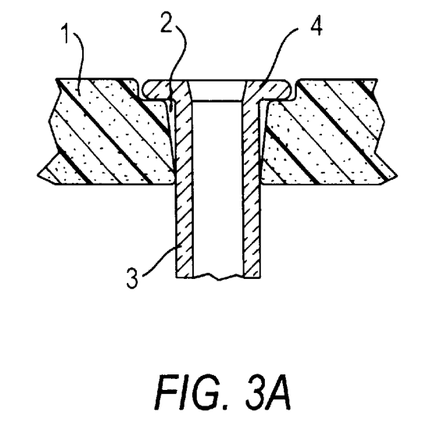
FIGS. 3A, 3B, 3C and 3D are respective cutaway cross-sectional views through four additional different embodiments of the carrier plate of the invention with respective different clamping seats for containers in the form of syringes with finger supports held in through-going holes provided in the carrier plates, in which the finger supports are sunk in the surface of the carrier plate.
Figure 3B:
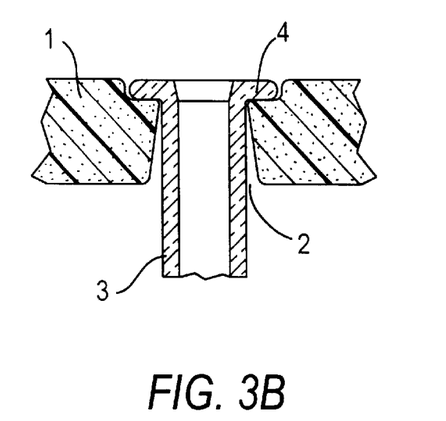

As shown in FIGS. 2B and 2C for a syringe body 3, whose finger support 4 protrudes from the opening 2 above the surface of the carrier plate 1 and for a syringe body 3 in FIGS. 3A and 3B, whose finger support 4 is flush with the upper surface of the carrier plate 1, the through-going openings 2 are conical, so that the inserted containers 3 are securely fixed and centered. Thus tolerances in the container geometry are compensated by the design of the openings or holes 2 in the carrier plate 1.

The conical interior surfaces of the openings can taper so as to constrict in a downward direction as in FIGS. 2B and 3A or upward as in FIGS. 2C and 3B.

FIGS. 2A to 2E and FIGS. 3A to 3D illustrate cross-sectional views through various embodiments of the carrier plate 1 in the vicinity of a through-going opening 2 for a container 3.

Figure 2D:
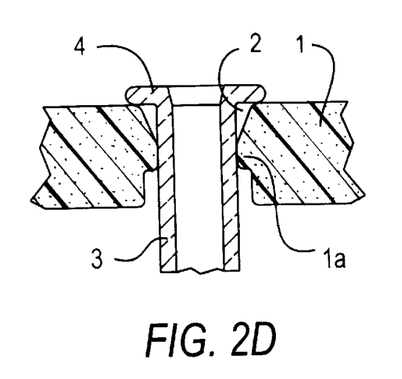
Figure 3C:
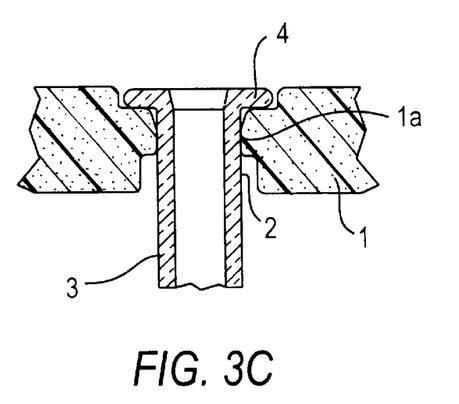

The containers 3 can be held clamped in the through-going openings 2 of the carrier plate 1, as shown in FIGS. 2D and 3C. The containers 3 in the embodiments shown in FIGS. 2D and 3C are held fixed by annular constricting or radially inwardly extending portions 1a of the carrier plate 1 that are formed within the openings 2 shown in the carrier plate 1. These annular constricting portions 1a are formed so that the inner diameter of the openings 2 at their narrowest is smaller than the outer diameter of the containers 3.

Figure 2E:
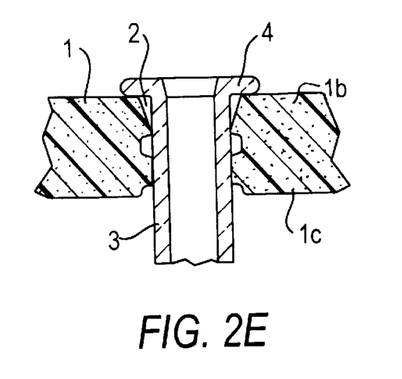
Figure 3D:
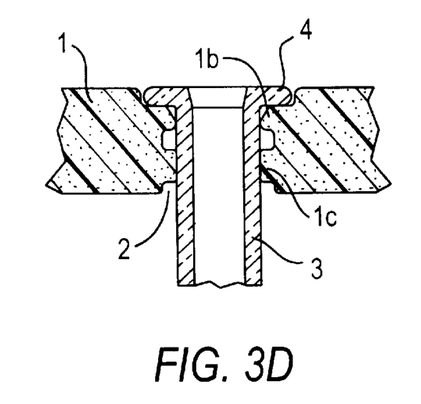

In the embodiments according to FIGS. 2E and 3D two axially spaced circumferential radially inwardly projecting or annular constricting portions 1b and 1c of the carrier plate 1 are formed within the opening 2. They fix and hold the containers 3 more securely in the through-going openings 2.

In a special embodiment of the carrier plate according to the invention the through-going holes 2 are formed so that the guiding and clamping of the containers 3 occurs at three edges (point projections), which improve the self-centering effect, and prevent thermal insulation of a portion of the container by the carrier plate material. These edges preferably are at different axial heights.

In another special embodiment the carrier plate i is made from a foamed plastic material, which was foamed with an inert gas (e.g. nitrogen, carbon dioxide, argon). This prevents the formation of ozone gas during sterilization by energetic radiation (γ radiation or electron radiation).

According to an embodiment of the invention the carrier plate made from foamed plastic material contains reinforcing elements 30.

In an alternative embodiment the carrier plate 1 has a rib structure 30 or geometry for the purpose of stiffening it.

Preferably the carrier plate contains additional holes and/or openings 20 for reducing the outflow resistance, which is important in working in a clean room and in autoclaving.

The carrier plate 1 must not necessarily comprise a foamed plastic plate, although this is the preferred embodiment. It can also be injection molded. When it is injection molded the holes or openings are then clad with circular jackets of foamed plastic material.

The carrier plate 1 according to the invention can be used in the most different handling methods for manufacturing and filling containers 3. It is also useable as an insert in a vat-like vessel as a transport unit for empty or filled containers 3.

In a special embodiment the carrier plate 1 in a stepped or stair-like structure in which the container ends, as seen in a vertical direction, are found at different heights, so that e.g. a syringe with a large finger support does not contact the adjacent finger support.

A one-piece carrier plate 1 is shown in FIGS. 1 to 3. In an alternative embodiment the carrier plate 1 comprises several layers, e.g. at least one PE layer and a foamed layer from PP or PET. The holding devices are formed in the foamed layer and the PE layer is provided to improve the stiffness or rigidity of the carrier plate 1. Instead of a PE layer other plastic layers, for example a polystyrene (PS) or polypropylene (PP) or the like layer, can be used.

Figure 4:
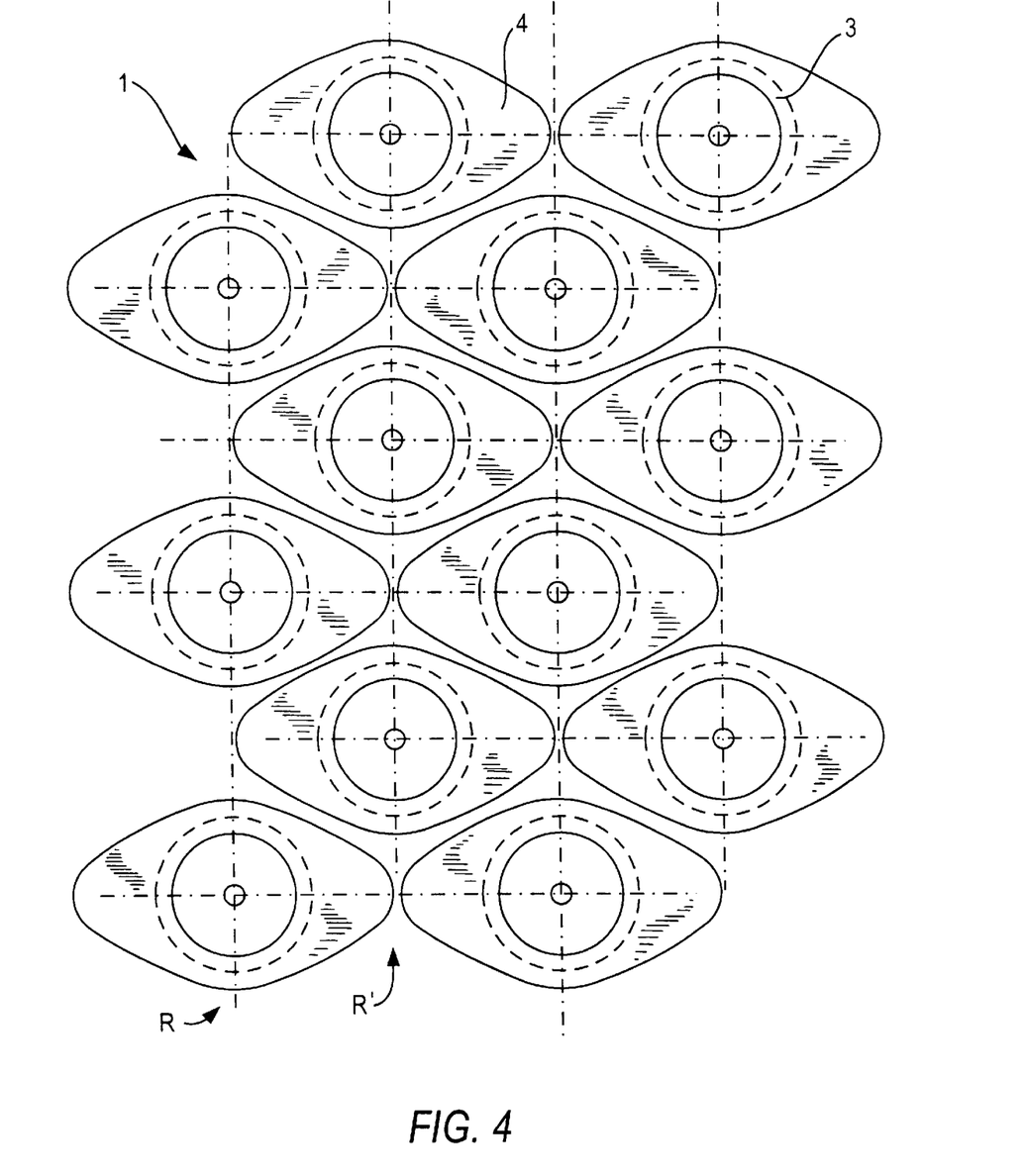
FIG. 4 is a diagrammatic top plane view of the carrier plate according to the invention equipped with containers in the form of syringes with finger supports each having a parabolic outer contour on opposite sides.

FIG. 4 shows an embodiment of the carrier plate 1 with several hole rows R,R' displaced or staggered with respect to each other, so that a very high packing density can be obtained for syringes with specially formed parabolic shaped finger supports 4. This embodiment is especially economical for manufacturing and filling the syringe bodies and thus reduces costs.

FIGS. 2A to 4 show embodiments of the invention, in which containers 3 formed as injector bodies or syringe bodies are suspended clamped with their finger supports (gripping members) 4 in the carrier plate 1. FIGS. 5 and 6 show embodiments of the carrier plate 1 for receiving containers 3 in the form of flasks or bottles.

Figure 5A:
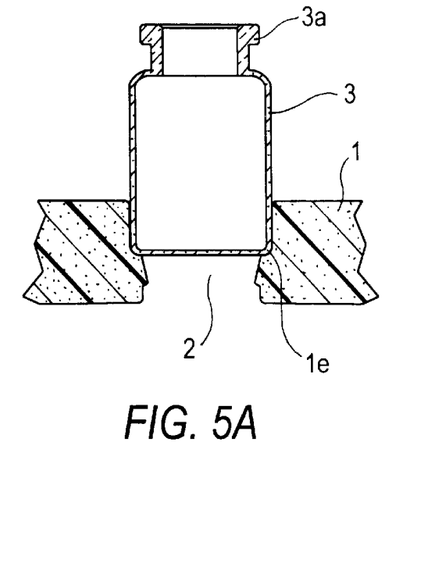
FIGS. 5A, 5B, 5C and 5D are respective cutaway cross-sectional views showing flasks inserted in form-locking clamping seats provided in carrier plates according to the invention.

FIG. 5A shows an upwardly standing bottle 3, which has peripheral lip 3a on its closure end 3a, held in the carrier plate 1. The through-going opening 2 in the carrier plate has a correspond shoulder 1e for gripping and holding the bottle base or bottom.

Figure 5B:
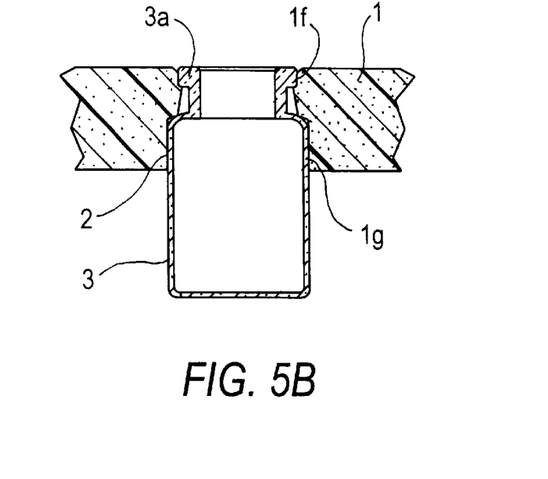

FIG. 5B shows a similar bottle held in another embodiment of the carrier plate 1 so that its peripheral lip 3a is held flush with the upper surface of the carrier plate 1 by means of a shoulder 1f in the through-going hole 2. The upper cylindrical portion of the bottle is also held in a form-locking manner in the cylindrical section 1g of the opening or hole 2. The bottle 3 is inserted in the holding device according to FIG. 5B from below in the opening or hole 2 of the carrier plate 1, until the peripheral lip 3a locks on the shoulder 1f. Then it is suspended from this shoulder 1f and of course without tilting because of the guidance provided by the cylindrical section 1g of the opening 2.

Figure 5C:
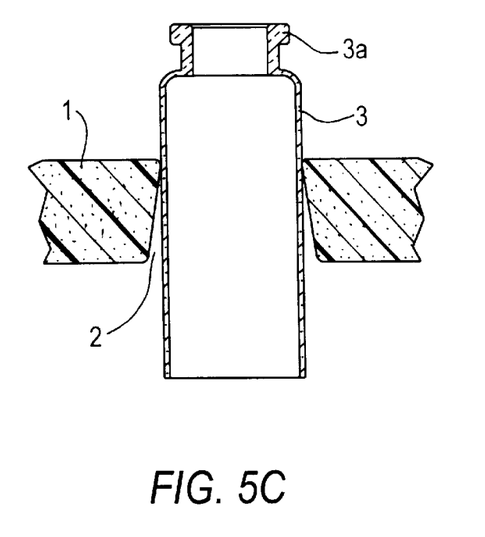

A somewhat elongated bottle 3 is held clamped in a conical through-going opening 2 in the carrier plate 1 shown in FIG. 5C. This holding device is similar to that for the syringe body 3 shown in FIG. 2C.

Figure 5D:
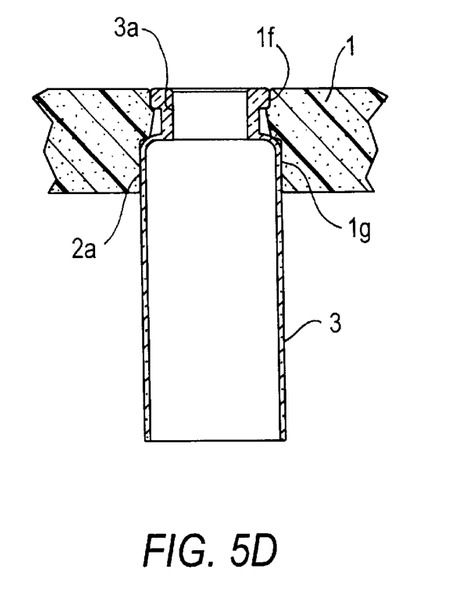

The holding device for the elongated bottle 3 shown in FIG. 5D is similar to the form-locking holding device shown in FIG. 5B with the peripheral lip 3a engaged on the shoulder 1f.

FIGS. 6A to 6D show four additional embodiments for the holding device for the bottles 3 in the through-going openings 2 of the carrier plate 1 according to the invention. The through-going openings 2 have an inner diameter that conforms to the diameter of the outer diameter of the bottle. These holding devices include several, preferably three, flexible lip elements 1h formed at the opening 2.

Figure 6A:
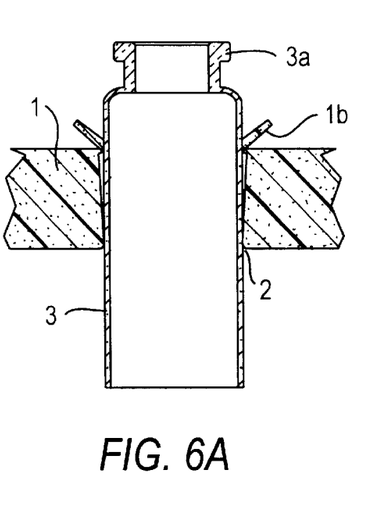
FIGS. 6A, 6B, 6C and 6D are respective cutaway cross-sectional views of different holding devices for flasks or bottles including molded lips provided on the edges of the through-going holes provided in the carrier plate according to the invention.
Figure 6B:
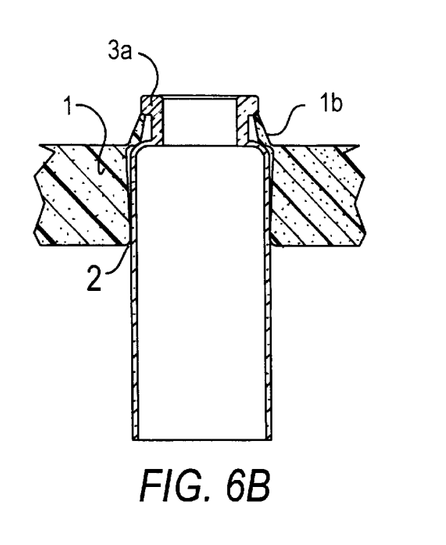

According to FIGS. 6A and 6B the bottle is inserted from above in the through-going openings 2 until the lip 1h engages on the rear portion of the peripheral lip 3a.

Figure 6C:
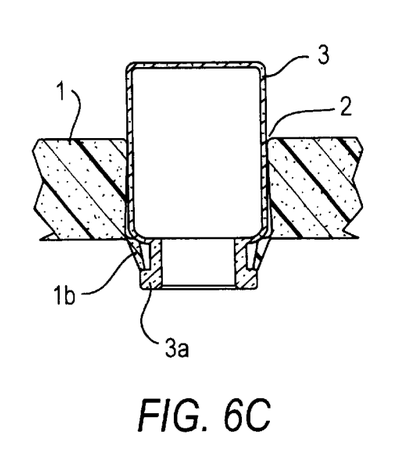
Figure 6D:
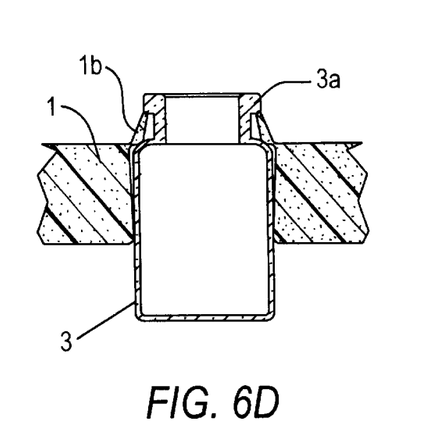

FIG. 6D shows the same holding device as in FIG. 6B but for a shorter thicker bottle 3, i.e. a bottle 3 is held clamped with the lip 1h on the rear portion of the peripheral lip 3a and with the bottle jacket held in the passage 2. The FIG. 6C shows a similar upper held holding device for the same bottle 3.

The invention provides a universal transport device for medicinal containers, especially for packaging medicinal substances, independently of their cross-section, having the following advantageous properties:

- simple, i.e. few parts
- fixing and centering of the containers independently of protruding portions (e.g. finger supports on finished syringes), i.e. also suitable for cylindrical ampoules, ampoules, flasks, glass cylinders, which have no protruding portions
- no moving parts
- economical to manufacture
- suitable for one-time uses
- sterilizable, e.g. by energetic radiation, sterilizing gases, such as ethylene oxide or autoclaving (121° C. steam)
- simultaneous transport protection
- useable in freeze-dry units.

While the invention has been illustrated and described as embodied in a transport device for medicinal containers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A device for transporting, filling and sterilizing medicinal containers, said device comprising a rigid foamed plastic carrier plate (1) having a pore-free sealed surface to facilitate sterilization;

wherein said rigid foamed plastic carrier plate is provided with a plurality of first openings (2) for receiving said medicinal containers (3) and a plurality of second openings (20) to facilitate sterilizing, said second openings (20) being formed smaller than said first openings so that said medicinal containers (3) cannot be received in said second openings; and wherein said rigid foamed plastic carrier plate (1) has a predetermined thickness and said first openings (2) have respective open cross-sections adapted to corresponding cross-sections of said medicinal containers, so that, when said medicinal containers are inserted in said first openings (2), said medicinal containers (3) are clamped, centered and held fixed in said first openings without causing rattling of said medicinal containers (3) during said transporting, filling and sterilizing, whereby no scratch marks are produced on said medicinal containers and no static charges are produced on said medicinal containers.

2. The device as defined in claim 1, wherein said first openings (2) are arranged in rows (R) and adjacent rows are displaced or shifted with respect to each other by one half a distance between neighboring first openings (2) in one of said adjacent rows.

3. The device as defined in claim 2, wherein said carrier plate (1) is a one-piece plate.

4. The device as defined in claim 2, wherein said carrier plate (1) is a multi-layer plate.

5. The device as defined in claim 2, wherein said rigid foamed plastic carrier plate (1) consists of a plastic material selected from the group consisting of foamed polypropylenes and foamed polyesters.

* * * * *